US00PP11200P

United States Patent [19]

Fruehwirth

[11] Patent Number: Plant 11,200

[45] Date of Patent: Feb. 1, 2000

[54] POINSETTIA PLANT NAMED 'ECKABISH'

[75] Inventor: Franz Fruehwirth, Encinitas, Calif.

[73] Assignee: Paul Ecke Ranch, Inc., Encinitas, Calif.

[21] Appl. No.: 09/003,915

[22] Filed: Jan. 7, 1998

[51] Int. Cl.[7] ..... A01H 5/00

[52] U.S. Cl. ..... Plt./307

[58] Field of Search ..... Plt./307

[56] References Cited

U.S. PATENT DOCUMENTS

P.P. 7,275 7/1990 Fruehwirth ..... Plt./307

*Primary Examiner*—Howard J. Locker
*Assistant Examiner*—Kent L. Bell
*Attorney, Agent, or Firm*—Arnold White & Durkee

[57] ABSTRACT

Poinsettia 'Eckabish' is a new cultivar, distinguished by bright raspberry red flower bracts, dark green foliage, self-branching characteristics, and 8-week flowering response time. The primary flower bracts are dentate to serrate and the flower clusters are prominent. The new plant produces a very desirable branched flowering pot plant for the holiday season market. 'Eckabish' is resistant to epinasty after being confined to shipping containers. The post-production foliage and bract retention is excellent even under low light intensities in the consumer's home.

1 Drawing Sheet

BACKGROUND OF THE PLANT

This new Poinsettia cultivar, 'Eckabish', originated as an induced self-branching sport of a seedling known as 'R-26' (not patented) in my greenhouse in Encinitas, Calif. 'R-26' is a proprietary plant and there are no specimens in the public domain. 'Eckabish' was selected because of its bright, raspberry red flower bracts, large flower clusters, dark green foliage, early-season flowering response and self branching characteristics; traits which distinguish it from other poinsettia cultivars, and seem to make it a desirable plant for commercial greenhouse production. After selection, 'Eckabish' was vegetatively reproduced from stem cuttings for test purposes in Encinitas, Calif. By subjecting clones of this plant to successive generations of vegetative propagation, it was demonstrated that the distinctive characteristics of 'Eckabish' held true from generation to generation.

BRIEF DESCRIPTION OF THE PHOTOGRAPHS

Poinsettia 'Eckabish' is illustrated in the accompanying color photographs.

The upper photograph is a side view of one branched plant per pot in full flower.

The lower photograph is a top view of the same plant showing flower and bract formation.

DESCRIPTION OF THE PLANT

The following is a detailed description of this new poinsettia as observed in Encinitas, Calif., U.S.A. during December 1996. Observations were recorded from flowering plants, grown as one branched plant per pot. The pot was 14 cm. in diameter and 11 cm. in height. Color designations are compared to the 1986 edition of R.H.S. Colour Chart, first published in 1966 by The Royal Horticultural Society, London, England.

THE PLANT

Origin: Sport of a seedling. The sport was induced by application of the procedures set forth in U.S. Pat. No. 4,724,276 to the seedling parent plant. Rootstock used was 'Dark Red Hegg' U.S. Plant Pat. No. 3,160).

Classification:

*Botanic.*—*Euphorbia pulcherrima* Willd.

*Common name.*—Poinsettia.

*Cultivar name.*—'Eckabish'.

Form: Shrub.

Height: Short to medium.

Growth Habit: As a single stemmed plant, upright and vigorous with self-branching side shoots. The application of a chemical growth retardant may not be needed to restrict height for commercial pot plant production. I observed one branched plant in a pot with an overall height of 38 cm and an overall width of 46 cm. The diameter of individual inflorescences is 26 cm.

Branching: Axillary branches will develop and terminate in an inflorescence without pinching. However, it is usually desirable to pinch 'Eckabish' before flower induction and remove all terminal dominance. Then, all axillary branches will develop uniformly and at a faster rate.

Growth rate: Rooting of stem cutting occurs in 12–18 days under intermittent mist. The plant will flower in about eight weeks under continuous long night conditions and night temperatures of about 16–18 degrees C.

Foliage: The foliage is clean and uniformly dark green from bottom to top of the plant. The leaves are of medium size, leaf blades typically being 11–12 cm long and 9–10 cm wide with dark red leaf petioles 5–6 cm long. Upper leaf surface is slightly rugose and the under surface is pubescent.

*Leaf shape.*—Typical leaves are ovate with acute to obtuse bases and acuminate tips. Leaf margins are mostly dentate with 2 lobes on each side of the leaf blade.

*Color.*—Upper side — Dark green, much darker than R.H.S. 139A. Under side — Green, R.H.S. 147A–B.

*Retention.*—The foliage lasts extremely well even under low light intensities in the consumer's home.

Bracts: Generally there are 24–27 raspberry red bracts of various sizes subtending the cyathia. The primary bracts have blades typically 11 cm long and 8 cm wide with petioles about 3 cm long

*Shape.*—Primary bracts are ovate with acute bases and acuminate tips. Bract margins are dentate to serrate. Secondary bracts of various sizes are broadly elliptic. Secondary bract margins are entire.

*Color.*—Upper side — Raspberry red, R.H.S. 47A–53B. Under side — Reddish, R.H.S. 53B–C.

Flowers: Generally, 20–22 cyathia (flowers) per inflorescence are present when the plant is in full bloom. Each cyathium is about 6 mm long and 6 mm wide, green in color, and fringed light red at the distal end. One yellow nectar cup protrudes from the side of each cyathium. The flower pedicel is also green and about 5 mm in length. The stamens protruding from the cyathia are dark red. The anthers are bifurcate; the pollen is yellow and copious. The stigmas are dark red and trifurcate.

*Cyathium.*—Cyathium retention is better than average, lasting three weeks beynd fully mature flowers.

*Nectar exudate.*—Abundant.

*Seeds.*—Self-incompatible.

*Fertility.*—Not observed.

Post production: Poinsettia 'Eckabish' is resistant to epinasty after being confined to shipping containers and retains its leaves and flower bracts for several weeks in the consumer's home environment.

Disease resistance: Typical of the species.

What is claimed is:

1. A new and distinct Poinsettia plant, substantially as herein shown and described, distinguished by its bright raspberry red flower bracts, dark green foliage, self-branching characteristics, early-season flowering response, dentate to serrate primary flower bracts, and prominent flower clusters.

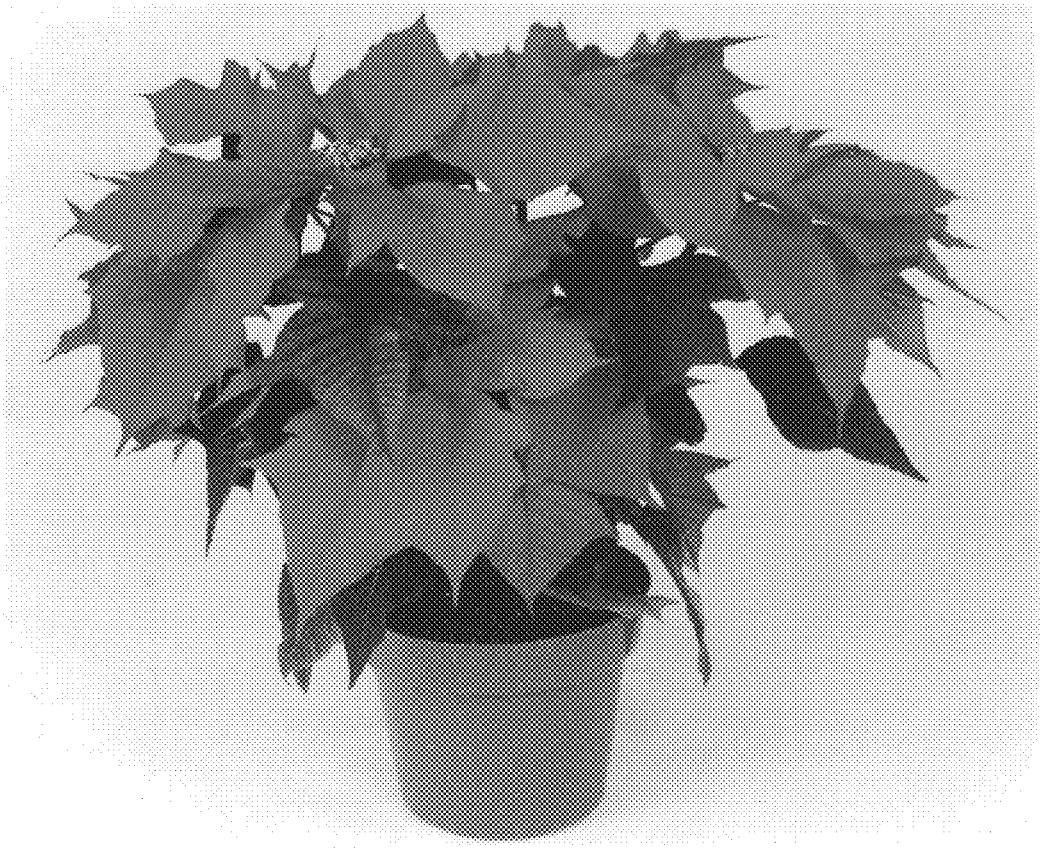
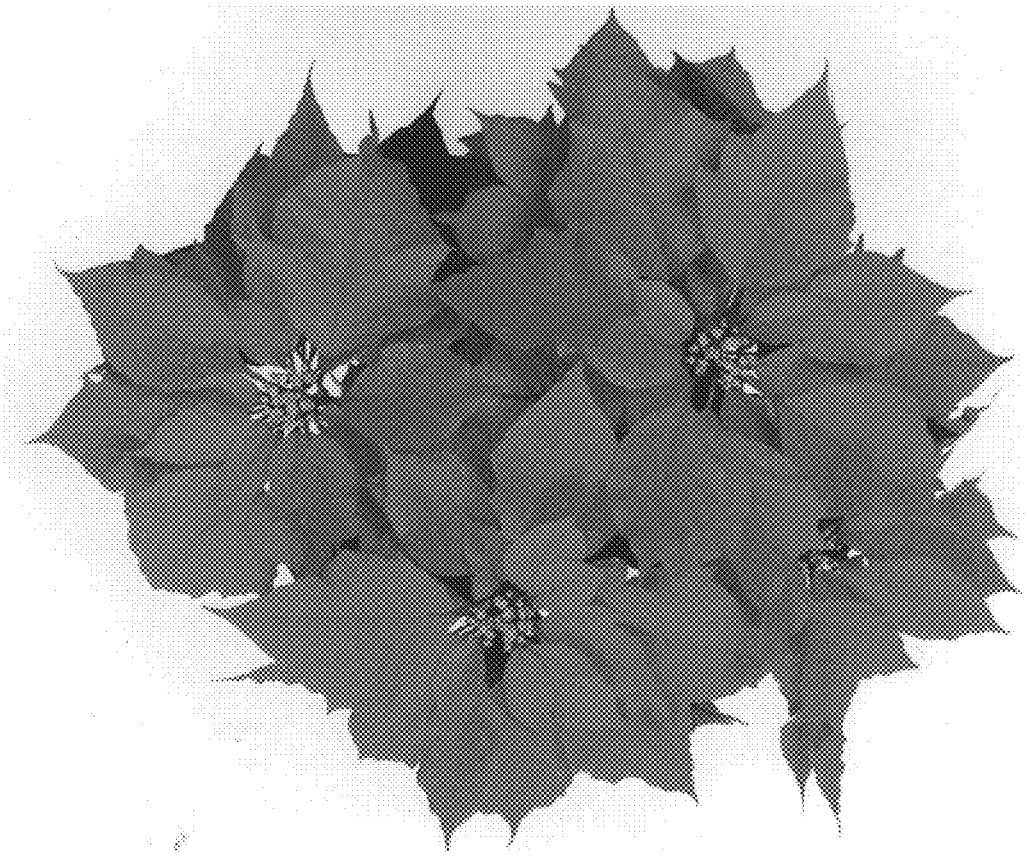

* * * * *